US011952329B2

(12) United States Patent
Tanaka et al.

(10) Patent No.: US 11,952,329 B2
(45) Date of Patent: Apr. 9, 2024

(54) PRODUCT 1,3-BUTYLENE GLYCOL

(71) Applicant: KH Neochem Co., Ltd., Tokyo (JP)

(72) Inventors: Hirotaka Tanaka, Kanagawa (JP); Takashi Hakumura, Mie (JP); Jun Kanada, Mie (JP)

(73) Assignee: KH NEOCHEM CO., LTD., Tokyo (JP)

( * ) Notice: Subject to any disclaimer, the term of this patent is extended or adjusted under 35 U.S.C. 154(b) by 0 days.

(21) Appl. No.: 18/556,453

(22) PCT Filed: Jun. 2, 2022

(86) PCT No.: PCT/JP2022/022426
§ 371 (c)(1),
(2) Date: Oct. 20, 2023

(87) PCT Pub. No.: WO2022/255436
PCT Pub. Date: Dec. 8, 2022

(65) Prior Publication Data
US 2024/0083830 A1    Mar. 14, 2024

(30) Foreign Application Priority Data

Jun. 4, 2021  (JP) ................................ 2021-094284

(51) Int. Cl.
*C07C 31/20* (2006.01)
*C07C 29/74* (2006.01)
*B01D 15/08* (2006.01)
*G01N 30/02* (2006.01)

(52) U.S. Cl.
CPC ............ *C07C 31/207* (2013.01); *C07C 29/74* (2013.01); *C07C 31/20* (2013.01); *B01D 15/08* (2013.01); *G01N 30/02* (2013.01); *G01N 2030/027* (2013.01)

(58) Field of Classification Search
CPC ....... C07C 31/20; C07C 31/207; C07C 29/74; B01D 15/08; G01N 30/02; G01N 2030/027
See application file for complete search history.

(56) References Cited

U.S. PATENT DOCUMENTS

| | | | |
|---|---|---|---|
| 6,376,725 B1 * | 4/2002 | Tsuji | ...................... C07C 31/20 568/853 |
| 8,445,733 B1 | 5/2013 | Windhorst et al. | |
| 2003/0018224 A1 | 1/2003 | Tsuji et al. | |
| 2004/0254407 A1 | 12/2004 | Mizutani et al. | |
| 2021/0101855 A1 | 4/2021 | Khandurina et al. | |

FOREIGN PATENT DOCUMENTS

| | | |
|---|---|---|
| JP | 8-21829 | 1/1996 |
| JP | 2001-213825 A | 8/2001 |
| JP | 2001-213828 A | 8/2001 |
| JP | 2001-288131 A | 10/2001 |
| JP | 2003-096006 A | 4/2003 |
| JP | 2020-512351 A | 4/2020 |
| JP | 2021-038189 A | 3/2021 |
| JP | 2021-042214 A | 3/2021 |
| WO | WO 00/07969 | 2/2000 |

OTHER PUBLICATIONS

International Search Report of the International Searching Authority directed to related International Patent Application No. PCT/JP2022/255436, dated Aug. 16, 2022, with attached English-language translation; 6 pages.
Decision to Grant from priority Japanese patent application No. 2021-094284, dated May 6, 2022, and machine translation, 5 pages.
Notice of Reasons for Refusal from priority Japanese patent application No. 2021-094284, dated Jan. 14, 2022, and machine translation, 6 pages.

* cited by examiner

*Primary Examiner* — Yate' K Cutliff
(74) *Attorney, Agent, or Firm* — Sterne, Kessler, Goldstein & Fox P.L.L.C.

(57) ABSTRACT

A product 1,3-butylene glycol, wherein, in an HPLC analysis under specific conditions after specific sample preparation, when a relative retention time of 2,4-dinitrophenylhydrazine is regarded as 1.0, a sum area value of absorbance peaks that appear within a relative retention time range of 4.4 to 12.0 is 1000 or less, and wherein
 a dinitrophenylhydrazine derivative of a carbonyl compound having 4 to 6 carbon atoms is contained as a component that corresponds to the peaks that appear within the relative retention time range of 4.4 to 12.0.

3 Claims, No Drawings

PRODUCT 1,3-BUTYLENE GLYCOL

TECHNICAL FIELD

The present invention relates to a product 1,3-butylene glycol that is useful as a raw material of synthetic resins, a raw material of surfactants, a solvent, an antifreeze, a cosmetic raw material or the like.

BACKGROUND ART 1,3-Butylene glycol is a viscous, colorless and transparent liquid having a low odor and a boiling point of 208° C. and has excellent chemical stability. Therefore, 1,3-butylene glycol is used as a raw material of a variety of synthetic resins and surfactants. 1,3-Butylene glycol is also utilized as a material for cosmetics, moisture absorbers, high-boiling point solvents and antifreezes by taking advantage of its excellent moisture absorption characteristic, low volatility and low toxicity. Particularly, in recent years, the demand for 1,3-butylene glycol has been significantly growing in the cosmetic industry since 1,3-butylene glycol having low toxicity and low stimulus has excellent properties as a moisturizer.

Patent Literature 1 discloses 1,3-butylene glycol having a weak odor. Furthermore, as a method for obtaining 1,3-butylene glycol having a weak odor, a production method of 1,3-butylene glycol including a step of mixing crude 1,3-butylene glycol with water and an organic solvent, phase-separating the mixture into a water layer and an organic layer and then obtaining a water layer containing 1,3-butylene glycol is disclosed. In the production method of the same literature, as the organic solvent that is used as an extraction solvent, ketones are considered to be favorable, and methyl isobutyl ketone is considered to be more preferable.

CITATION LIST

Patent Literature

Patent Literature 1: Japanese Patent Laid-Open No. 2003-96006

SUMMARY OF INVENTION

Technical Problem

However, in the method described in Patent Literature 1, there is a problem in that it is difficult to completely remove the odor and thus, when 1,3-butylene glycol is stored for a long period of time, a slight odor is generated due to a change over time.

Additionally, in the cosmetics field, 1,3-butylene glycol is directly applied to the skin for use, but 1,3-butylene glycol that is obtained by the method described in Patent Literature 1 has a problem that skin sensitization has not yet been sufficiently reduced.

In consideration of the above-described circumstances, an objective of the present invention is to provide a product 1,3-butylene glycol that is odorless, generates no odors over time, and additionally causes less skin sensitization.

Solution to Problem

As a result of intensive studies, the present inventors have found that the above-described problems can be solved by suppressing the concentration of a specific impurity that is contained in 1,3-butylene glycol at a certain level or lower and have completed the present invention.

More specifically, the present invention is as described below.

[1]

A product 1,3-butylene glycol wherein, in an HPLC analysis under the following conditions after the following sample preparation, when a relative retention time of 2,4-dinitrophenylhydrazine is regarded as 1.0, a sum area value of absorbance peaks that appear within a relative retention time range of 4.4 to 12.0 is 1000 or less, and wherein
  a dinitrophenylhydrazine derivative of a carbonyl compound having 4 to 6 carbon atoms is contained as a component that corresponds to the peaks that appear within the relative retention time range of 4.4 to 12.0, wherein the sample preparation is as follows:
  1000 µL of a solution of 2,4-dinitrophenylhydrazine which is extracted by adding 5 mL of acetonitrile to a 2,4-dinitrophenylhydrazine cartridge (InertSep mini AERO DNPH, GL Sciences Inc.) and 100 µL of 0.2 mol/L hydrochloric acid are added to 0.05 g of the product 1,3-butylene glycol and reacted at 45° C. for two hours, and wherein the conditions of HPLC analysis are as follows:
  measurement sample: a reaction liquid obtained by the sample preparation is diluted to 2 mL with a mobile phase that is used in HPLC, and the diluted liquid is used as a measurement sample,
  detector: UV-Vis detector,
  detection wavelength: 369 nm,
  analysis column: a column in which palmitamidopropyl group-modified silica gel (particle diameter: 5 µm, inner diameter×length=4.6 mm×25 cm, pore size: 100 Å, surface coating level: 2.7 µmol/m$^2$, surface area: 450 m$^2$/g, metal impurity: less than 5 ppm, carbon content: 19.5%) is used as a stationary phase,
  mobile phase: acetonitrile/distilled water=50/50 (volume ratio),
  mobile phase flow rate: 0.4 mL/min.,
  sample injection amount: 20 µL.

[2]

The product 1,3-butylene glycol according to [1], wherein the sum area value of the absorbance peaks that appear within the relative retention time range of 4.4 to 12.0 is 800 or less.

[3]

The product 1,3-butylene glycol according to [1], wherein the sum area value of the absorbance peaks that appear within the relative retention time range of 4.4 to 12.0 is 500 or less.

Advantageous Effects of Invention

The present invention makes it possible to provide a product 1,3-butylene glycol that is odorless, generates no odors over time, and additionally causes less skin sensitization.

DESCRIPTION OF EMBODIMENTS

Hereinafter, an embodiment of the present invention (hereinafter, referred to as "present embodiment") will be described in detail. The present invention is not limited to the following description and can be carried out after being modified in a variety of manners within the scope of the gist thereof.

In the present embodiment, 1,3-butylene glycol that is the final product will be also referred to as "product 1,3-butylene glycol", and 1,3-butylene glycol as a raw material will be also referred to as "crude 1,3-butylene glycol".

A product 1,3-butylene glycol according to the present embodiment is a product 1,3-butylene glycol in which, in an HPLC analysis under the following conditions after the following sample preparation, when a relative retention time of 2,4-dinitrophenylhydrazine is regarded as 1.0, a sum area value of absorbance peaks that appear within a relative retention time range of 4.4 to 12.0 is 1000 or less, and a dinitrophenylhydrazine derivative of a carbonyl compound having 4 to 6 carbon atoms is contained as a component that corresponds to the peaks that appear within the relative retention time range of 4.4 to 12.0.

Here, the dinitrophenylhydrazine derivative of a carbonyl compound having 4 to 6 carbon atoms is a compound obtained by derivatizing a carbonyl compound having 4 to 6 carbon atoms or acetal compounds thereof that is contained in 1,3-butylene glycol with 2,4-dinitrophenylhydrazine (hereinafter, also referred to as "DNPH"). Regarding these compounds, in an HPLC analysis under specific conditions to be described below, when the relative retention time of the peak of DNPH is regarded as 1.0, the peaks of the derivative appear within a relative retention time range of 4.4 to 12.0.

The measurement conditions of the HPLC analysis in the present embodiment are as described below.

[Sample Preparation]

1000 µL of a solution from which 2,4-dinitrophenylhydrazine has been extracted by adding 5 mL of acetonitrile to a 2,4-dinitrophenylhydrazine cartridge (InertSepmini AERO DNPH, GL Sciences Inc.) and 100 µL of 0.2 mol/L hydrochloric acid are added to 0.05 g of the product 1,3-butylene glycol and reacted at 45° C. for two hours.

[Conditions of HPLC Analysis]

Measurement sample: A reaction liquid that is obtained by the sample preparation is diluted to 2 mL with a mobile phase that is used in HPLC, and this diluted liquid is used as a measurement sample.

Detector: UV-Vis detector

Detection wavelength: 369 nm

Analysis column: A column in which palmitamidopropyl group-modified silica gel (particle diameter: 5 µm, inner diameter×length=4.6 mm×25 cm, pore size: 100 Å, surface coating level: 2.7 µmol/m$^2$, surface area: 450 m$^2$/g, metal impurity: less than 5 ppm, carbon content: 19.5%) is used as a stationary phase Analysis condition: Column temperature of 40° C.

Mobile phase: acetonitrile/distilled water=50/50 (volume ratio)

Mobile phase flow rate: 0.4 mL/min.

Sample injection amount: 20 µL

Here, as the analysis column, for example, SUPELCO® Ascentis® RP-Amide (particle diameter: 5 µm, inner diameter×length=4.6 mm×25 cm) manufactured by Merck KGaA can be used.

In the HPLC analysis, when the relative retention time of the peak of 2,4-dinitrophenylhydrazine is regarded as 1.0, the area values of absorbance at 369 nm of peaks that appear within a relative retention time range of 4.4 to 12.0 are measured with an ultraviolet spectrophotometer. In the product 1,3-butylene glycol of the present embodiment, in the HPLC analysis, when the relative retention time of 2,4-dinitrophenylhydrazine is regarded as 1.0, the sum area value of the absorbance peaks (hereinafter, also referred to as "the sum area value of the peaks") that appear within the relative retention time range of 4.4 to 12.0 is 1000 or less. When the sum area value of the peaks is 1000 or less, the generation of an odor and skin sensitization are reduced.

The sum area value of the peaks is preferably 800 or less, more preferably 500 or less and still more preferably 400 or less from the viewpoint of the effect of the present invention becoming more significant. The lower limit of the sum area value of the peaks is not particularly limited and may be, for example, 1 or more or may be 10 or more from the viewpoint of the production cost.

The product 1,3-butylene glycol of the present embodiment contains a dinitrophenylhydrazine derivative of a carbonyl compound having 4 to 6 carbon atoms as a component that corresponds to the peaks that appear within the relative retention time range of 4.4 to 12.0. Examples of the carbonyl compound having 4 to 6 carbon atoms include methyl ethyl ketone, methyl vinyl ketone, crotonaldehyde, butyraldehyde, isobutyraldehyde, methyl propyl ketone, methyl isopropyl ketone, diethyl ketone, 2-hexanone, 6-hexene-2-one, methyl isobutyl ketone, ethyl propyl ketone, ethyl isopropyl ketone and 1-hexanal. In the product 1,3-butylene glycol of the present embodiment, the amount of the carbonyl compound having 4 to 6 carbon atoms as an impurity is preferably small.

[Confirmation Method of Dinitrophenylhydrazine Derivative of Carbonyl Compound Having 4 to 6 Carbon Atoms]

As a method for confirming the relative retention time of the dinitrophenylhydrazine derivative of a carbonyl compound having 4 to 6 carbon atoms in the HPLC analysis, for example, the following method can be included. The relative retention time of the peak of the dinitrophenylhydrazine derivative of methyl vinyl ketone, crotonaldehyde or 2-hexanone to be detected can be confirmed by: adding 100 µL of 0.2 mol/L hydrochloric acid and 1000 µL of a solution extracted by adding 5 mL of acetonitrile to a DNPH cartridge (InertSep mini AERO DNPH, GL Sciences Inc.) to 0.05 g of a solution obtained by diluting methyl vinyl ketone manufactured by Tokyo Chemical Industry Co., Ltd., crotonaldehyde manufactured by Tokyo Chemical Industry Co., Ltd. or 2-hexanone manufactured by Fujifilm Wako Pure Chemical Corporation, all commercially available, with 1,3-butylene glycol manufactured by KH Neochem Co., Ltd.; reacting the mixture at 45° C. for two hours; diluting the resulting reaction solution with a mobile phase that is used in the HPLC to 2 mL; and injecting 20 µL of this diluted solution for measurement in the HPLC analysis under the above-described conditions.

In the product 1,3-butylene glycol of the present embodiment, the area percentage of the peak of 1,3-butylene glycol in a gas chromatography analysis under the following conditions (hereinafter, also referred to as GC analysis) is not particularly limited, but is, for example, preferably 99.6% or more, more preferably 99.7% or more, still more preferably 99.8% or more and particularly preferably 99.9% or more depending on required product qualities. The "area percentage" of a peak means the proportion of the area of the specific peak to the sum area of all peaks that appear in a chart. All peaks mean all peaks that appear in a case where the analysis is continued until the relative retention time reaches 2.2 and stopped when the relative retention time of the peak of 1,3-butylene glycol is regarded as 1.0. When the area percentage of the peak is within the above-described range, there is a tendency that the generation of an odor and skin sensitization are further reduced.

The measurement conditions of the gas chromatography analysis in the present embodiment are preferably as described below.

[Conditions of Gas Chromatography Analysis]

Analysis device: 7890B gas chromatography system manufactured by Agilent Technologies, Inc.

Analysis column: DB-WAX (length 30 m×inner diameter 0.25 mm×film thickness 0.25 μm) manufactured by Agilent Technologies, Inc.

Temperature rising conditions: The temperature was raised from 80° C. up to 230° C. at 5° C./minute and then retained at 230° C. for 10 minutes.

Sample introduction temperature: 250° C.

Carrier gas: Nitrogen

Gas flow rate in column: 0.5 mL/minute

Detector and detection temperature: Flame ionization detector (FID), 250° C.

Control mode: Constant flow

Split ratio: 50:1

Sample injection condition: 1 μL

[Skin Sensitization Test]

The product 1,3-butylene glycol in the present embodiment causes less skin sensitization. Here, the skin sensitization refers to the occurrence of an allergic reaction after the product 1,3-butylene glycol comes into contact with the skin. In the evaluation of skin sensitization, it has been common to use experimental animals, but the direct peptide reactivity assay (DPRA), which is an in Chemico test, was adopted as an alternative test in OECD guideline TG442C in 2015 from the viewpoint of animal welfare, and, in the present embodiment as well, the skin sensitization is evaluated by a test in which DPRA is used. In more detail, the skin sensitization is evaluated according to a method described in examples to be described below.

[Production Method of Product 1,3-Butylene Glycol]

(Raw Material)

Crude 1,3-butylene glycol that is used as a raw material at the time of producing the product 1,3-butylene glycol in the present embodiment is not particularly limited, and examples thereof include 1,3-butylene glycol from which an odor is sensed or 1,3-butylene glycol the odor of which becomes stronger over time. Alternatively, examples thereof also include 1,3-butylene glycol causing skin sensitization.

As the crude 1,3-butylene glycol as the raw material, the area percentage of the peak of 1,3-butylene glycol in a gas chromatography analysis under the above-described specific conditions is preferably 99.5% or more, more preferably 99.6% or more and still more preferably 99.7% or more from the viewpoint of reducing the amount of impurities that are contained in the product 1,3-butylene glycol.

A production method of the crude 1,3-butylene glycol as the raw material is not particularly limited, and the crude 1,3-butylene glycol can be produced by, for example, a well-known method (refer to Japanese Patent Publication No. H3-80139, Japanese Patent Laid-Open No. H7-258129 and the like). In addition, any of crude 1,3-butylene glycol produced by a liquid phase hydrogen reduction method of acetaldol, crude 1,3-butylene glycol produced by a hydrolysis method of 1,3-butylene oxide, crude 1,3-butylene glycol produced by a fermentation method in which a microbe or a fungus is used, a mixture thereof and the like may also be used. Among these, a reaction product obtained by the liquid phase hydrogen reduction method of acetaldol is preferably used since there is a tendency that the effect of the present invention becomes more significant. In the liquid phase hydrogen reduction method of acetaldol, low-boiling compounds such as acetaldehyde, butyraldehyde, crotonaldehyde, methyl vinyl ketone, or condensates of the low-boiling compounds, which are considered to be odor-causing substances, acetals of the low-boiling compounds and 1,3-butylene glycol, acetals of the low-boiling compound and ethanol or the like are generated as byproducts, and it is difficult to completely remove the low-boiling compounds or the like even by distillation. As the odor-causing substances, substances that act as odor sources, substances that turn into odor substances due to a change over time, a heating treatment, a chemical treatment or the like and the like are included.

The reaction product that is obtained by a hydrogen reduction method of acetaldol may also be used after alcohols such as ethanol, salts, moisture or the like, which are byproducts, are removed. A method for removing the above-described components is not limited, and a method such as distillation or adsorption can be used.

In addition, the reaction product that is obtained by the hydrogen reduction method of acetaldol from which ethanol or the like, which is a byproduct, has been removed by distillation or a substance obtained by further performing one or more well-known purification steps, for example, a step of adding an alkali metal compound (for example, sodium hydroxide, potassium hydroxide or the like) and performing a heating treatment (refer to Japanese Patent No. 4559625 or the like) on a distillate from which ethanol has been removed may also be used as the crude 1,3-butylene glycol. The crude 1,3-butylene glycol can also be procured as a commercially available product.

A production method of the product 1,3-butylene glycol in the present embodiment is not particularly limited, and it is possible to use, for example, a method including a step of performing a heating treatment on the crude 1,3-butylene glycol (heating treatment step), a step of mixing the crude 1,3-butylene glycol that has been subjected to the heating treatment with water and an organic solvent, phase-separating the mixture into a water layer and an organic layer and then obtaining a water layer containing 1,3-butylene glycol (extraction step), a step of distilling water away from the water layer containing the 1,3-butylene glycol (dehydration with distillation step) and a step of distilling low-boiling point components away from 1,3-butylene glycol from which water has been distilled away (low-boiling fraction distillation step). Hereinafter, each step will be described.

(Heating Treatment Step)

The heating treatment step in the production method of the product 1,3-butylene glycol of the present embodiment is a step of performing a heating treatment on the crude 1,3-butylene glycol. When a heating treatment is performed on the crude 1,3-butylene glycol, since the heating decomposition of highly polar impurities such as the carbonyl compounds having 4 to 6 carbon atoms, which are highly compatible with 1,3-butylene glycol, progresses, and the impurities turn into medium-polar dehydration condensates or acetal compounds, it is presumed that the impurities are efficiently removed in the subsequent extraction step. However, the mechanism of the present invention is not limited to what has been described above.

The heating time in the heating treatment step is not particularly limited, but is preferably 20 minutes to nine hours, more preferably one to six hours and still more preferably one to three hours. When the heating time is 20 minutes or longer, there is a tendency for the heating decomposition of the highly polar impurities to sufficiently progress, and, when the heating time is nine hours or shorter, there is a tendency that an increase in the cost taken for the heating treatment can be suppressed.

The heating temperature in the heating treatment step is not particularly limited, but is preferably 120° C. to 200° C., more preferably 130° C. to 170° C. and still more preferably 140° C. to 160° C. When the heating temperature is 120° C. or higher, there is a tendency for the heating decomposition of the highly polar impurities to sufficiently progress, and, when the heating temperature is 200° C. or lower, a heating decomposition reaction of 1,3-butylene glycol is suppressed, and there is a tendency that the impurities reduce.

A heating treatment device in the heating treatment step is not particularly limited, examples thereof include heating treatment devices such as a continuous tube-type device, a batch tank-type device and a continuous tank-type device, and, in a case where the batch method is used, the batch tank-type device is particularly preferable from the viewpoint of the stirring efficiency.

(Extraction Step)

The extraction step in the production method of the product 1,3-butylene glycol of the present embodiment is a step of mixing the crude 1,3-butylene glycol that has been subjected to the heating treatment with water and an organic solvent, phase-separating the mixture into a water layer and an organic layer and then obtaining a water layer containing 1,3-butylene glycol. Here, examples of the organic solvent include aliphatic hydrocarbons such as hexane and heptane, cycloaliphatic hydrocarbons such as cyclohexane and methylcyclohexane, aromatic hydrocarbons such as toluene and xylene, ethers such as diethyl ether and dibutyl ether, organic chlorides such as methylene chloride and chloroform, esters such as ethyl acetate and butyl acetate and ketones such as methyl isobutyl ketone, and, among these, ketones or cycloaliphatic hydrocarbons are preferable, and methyl isobutyl ketone or methylcyclohexane is more preferable from the viewpoint of impurity removal. These organic solvents may be used singly or two or more organic solvents may be selected, mixed in an arbitrary ratio and used. The amount of the organic solvent used is preferably 10 to 300 parts by mass and more preferably 20 to 200 parts by mass with respect to 100 parts by mass of the crude 1,3-butylene glycol that has been subjected to the heating treatment from the viewpoint of the extraction efficiency.

The amount of water used is preferably 20 to 400 parts by mass and more preferably 40 to 200 parts by mass with respect to 100 parts by mass of the crude 1,3-butylene glycol that has been subjected to the heating treatment from the viewpoint of the extraction efficiency. The order of adding water and the organic solvent to the crude 1,3-butylene glycol that has been subjected to the heating treatment is not particularly limited. The temperature at which water and the organic solvent are mixed with the crude 1,3-butylene glycol that has been subjected to the heating treatment is not particularly limited, but is preferably a temperature of 5° C. to 80° C. and more preferably a temperature of 10° C. to 50° C. from the viewpoint of the extraction efficiency.

The crude 1,3-butylene glycol that has been subjected to the heating treatment, water and the organic solvent can be mixed by, for example, a batch method, a continuous method or the like. Examples of the case of mixing by a batch method include a form in which the crude 1,3-butylene glycol that has been subjected to the heating treatment, water and the organic solvent are put into a mixing tank, preferably stirred for 10 seconds to two hours and then preferably placed still for one minute to two hours to be phase-separated and a water layer containing 1,3-butylene glycol is obtained and the like. The operation of further adding the organic solvent to the obtained water layer containing 1,3-butylene glycol and stirring the mixture to separate phases and then obtaining the water layer containing 1,3-butylene glycol may be repeated, and the number of repetitions is preferably once to three times. In this case, the amount of the organic solvent added per operation is preferably 10 to 300 parts by mass with respect to 100 parts by mass of the crude 1,3-butylene glycol that has been subjected to the heating treatment.

As a device in the case of mixing by a continuous method, devices that are ordinarily used for continuous extraction or the like, for example, a combination of a mixer and a settler, a spray tower, a packed tower, a tray tower and the like can be used, and, in particular, a packed tower or tray tower having three or more theoretical plates is preferably used.

(Dehydration with Distillation Step)

The dehydration with distillation step in the production method of the product 1,3-butylene glycol of the present embodiment is a step of distilling water away from the water layer containing 1,3-butylene glycol obtained in the extraction step. Examples of a distillation device that is used in the dehydration with distillation step include a perforated plate tower, a bubble cap tower and a packed tower, and, among these, a packed tower having seven to 40 theoretical plates is preferable. The distillation tower may be one tower, or two or more towers may be used. As the distillation conditions, the pressure at the tower top portion of the distillation tower is preferably 5 to 20 kPa, and the temperature at the tower bottom portion of the distillation tower is preferably 120° C. to 160° C. and more preferably 135° C. to 155° C. Examples of a specific aspect of the dehydration with distillation step include a method in which the water layer containing 1,3-butylene glycol is continuously supplied from the tower top of the distillation tower, a distillate containing a large amount of water is continuously extracted from the tower top and, simultaneously, 1,3-butylene glycol is continuously extracted from the tower bottom.

(Low-Boiling Fraction Distillation Step)

The low-boiling fraction distillation step in the production method of the 1,3-butylene glycol of the present embodiment is a step of distilling the low-boiling point components away from 1,3-butylene glycol obtained in the dehydration with distillation step. Examples of a distillation device that is used in the low-boiling fraction distillation step include a perforated plate tower, a bubble cap tower and a packed tower, and, among these, a packed tower having seven to 40 theoretical plates is preferable. The distillation tower may be one tower, or two or more towers may be used. As the distillation conditions, the pressure at the tower top portion of the distillation tower is preferably 1 to 20 kPa, and the temperature at the tower bottom portion of the distillation tower is preferably 100° C. to 160° C. and more preferably 110° C. to 140° C. Examples of a specific aspect of the low-boiling fraction distillation step include a method in which 1,3-butylene glycol is continuously supplied from the tower top of the distillation tower, a distillate containing a large amount of the low-boiling point components is continuously extracted from the tower top and, simultaneously, 1,3-butylene glycol is continuously extracted from the tower bottom.

As a production method of 1,3-butylene glycol in the present embodiment, a method in which the preferable ranges of the above-described individual steps are combined together is preferable.

EXAMPLES

Hereinafter, the present invention will be more specifically described with examples, but the present invention is not limited to the following examples. As crude 1,3-butylene glycol that acted as a raw material, 1,3-butylene glycol manufactured by KH Neochem Co., Ltd. (product name: 1,3-butylene glycol) was used. A variety of analyses and evaluations were performed according to the following.

[HPLC Analysis]

Under the following conditions, an HPLC analysis of a product 1,3-butylene glycol was performed.

(Conditions of HPLC Analysis)

Sample preparation: 1000 μL of a solution from which 2,4-dinitrophenylhydrazine had been extracted by adding 5 mL of acetonitrile to a 2,4-dinitrophenylhydrazine cartridge (InertSep mini AERO DNPH, GL Sciences Inc.) and 100 μL of 0.2 mol/L hydrochloric acid were added to 0.05 g of 1,3-butylene glycol and reacted at 45° C. for two hours. The reaction liquid was diluted to 2 mL with a mobile phase that was used in HPLC, and this diluted liquid was used as a measurement sample.

Analysis device: Agilent 1200 Series manufactured by Agilent Technologies, Inc.

Detector: Agilent 1200 Series UV-Vis detector G1314B manufactured by Agilent Technologies, Inc.

Detection wavelength: 369 nm

Analysis column: SUPELCO® Ascentis® RP-Amide (particle diameter: 5 μm, inner diameter×length=4.6 mm×25 cm) manufactured by Merck KGaA Analysis condition: Column temperature of 40° C.

Mobile phase: Acetonitrile/distilled water=50/50 (volume ratio)

Mobile phase flow rate: 0.4 mL/min.

Sample injection condition: 20 μL

SUPELCO® Ascentis® RP-Amide manufactured by Merck KGaA used as the analysis column is a column in which palmitamidopropyl group-modified silica gel (particle diameter: 5 μm, inner diameter×length=4.6 mm×25 cm, pore size: 100 Å, surface coating level: 2.7 μmol/m$^2$, surface area: 450 m$^2$/g, metal impurity: less than 5 ppm, carbon content: 19.5%) is used as a stationary phase.

In measurement of the sample prepared by the above-described method, the area values of absorbance at 369 nm of peaks that appeared within a relative retention time range of 4.4 to 12.0 when the relative retention time of the peak of 2,4-dinitrophenylhydrazine was regarded as 1.0 were measured with an ultraviolet spectrophotometer. The fact that dinitrophenylhydrazine derivatives of carbonyl compounds having 4 to 6 carbon atoms were contained as components that corresponded to the peaks that appeared within the relative retention time range of 4.4 to 12.0 when the relative retention time of the peak of 2,4-dinitrophenylhydrazine was regarded as 1.0 was confirmed by the above-described confirmation method.

[Gas Chromatography Analysis]

Under the following conditions, a gas chromatography analysis of the product 1,3-butylene glycol, which was a subject, was performed.

(Conditions of Gas Chromatography Analysis)

Analysis device: 7890B gas chromatography system manufactured by Agilent Technologies, Inc.

Analysis column: DB-WAX (length 30 m×inner diameter 0.25 mm×film thickness 0.25 μm) manufactured by Agilent Technologies, Inc.

Temperature rising conditions: The temperature was raised from 80° C. up to 230° C. at 5° C./minute and then retained at 230° C. for 10 minutes.

Sample introduction temperature: 250° C.

Carrier gas: Nitrogen

Gas flow rate in column: 0.5 mL/minute

Detector and detection temperature: Flame ionization detector (FID), 250° C.

Control mode: Constant flow

Split ratio: 50:1

Sample injection condition: 1 μL

[Odor Test]

On 1,3-butylene glycol obtained in examples and a comparative example, an odor test was performed according to two evaluation methods described below.

(Evaluation Method of Odor)

10 g of a 10 weight % aqueous solution of 1,3-butylene glycol was put into a 20 mL wide mouth glass bottle, a lid was closed, and the aqueous solution was stirred hard at room temperature for one minute. The lid was opened, the odor was smelled and compared with a standard odor sample, and the odor level of the sample was determined. The number of evaluators was set to seven, and the average point of the evaluation results by the individual persons was calculated and used as a grade of the odor.

(Evaluation Method of Odor recurrence)

10 g of a 10 weight % aqueous solution of 1,3-butylene glycol was put into a 20 mL wide mouth glass bottle, a lid was closed, and the aqueous solution was heated at 50° C. for three days. After that, the aqueous solution was cooled to room temperature and stirred hard for one minute. The lid was opened, the odor was smelled and compared with a standard odor sample, and the odor level of the sample was determined. The number of evaluators was set to seven, and the average point of the evaluation results by the individual persons was calculated and used as a grade of the odor recurrence. The above-described test will be referred to as "the odor recurrence test".

Grades

A 10 weight % aqueous solution of 1,3-butylene glycol manufactured by KH Neochem Co., Ltd. was used as the standard odor sample, and the grade of the sample was determined as five. In a case where no odor was sensed, a grade 1 was given, and, in the other cases, grades 2 to 4 were given according to the following criteria.

1: No odor is sensed
2: An odor is faintly sensed
3: A weak odor is sensed
4: An odor is sensed
5: An odor is clearly sensed

[Skin Sensitization Test]

On 1,3-butylene glycol obtained in Examples 1 and 2 and Comparative Example 1, the skin sensitization was evaluated according to the following method.

(Conditions of Skin Sensitization Test)

15 mg of cysteine-containing peptide for DPRA manufactured by Scrum Inc. and 30 mL of a 0.05 M phosphate buffer were mixed together, thereby preparing a 0.05 M phosphate buffer solution containing 0.667 mM of the peptide (hereinafter, peptide solution). After one hour elapsed from the preparation of the peptide solution, 750 μL of the peptide solution and 250 μL of acetonitrile were put into each of three brown sample bottles for HPLC, thereby preparing three reference solutions. After two hours elapsed from the preparation of the reference solutions, 750 μL of the peptide solution, 200 μL of acetonitrile and 50 μL of 1,3-butylene glycol were put into a separate brown sample bottle for HPLC, thereby preparing a specimen solution (specimen solution 1). Furthermore, after four hours elapsed and six hours elapsed from the preparation of the reference solutions, specimen solutions were prepared by the same operation (specimen solution 2 and specimen solution 3). Each of the three reference solutions and the specimen solutions (specimen solution 1, specimen solution 2 and specimen solution 3) was measured by an HPLC analysis after 72±2 hours elapsed from the preparation of each solution, and the three-time average value of the peak heights of peptide in each of the reference solutions and the specimen solutions was calculated. A peptide reduction percentage was calculated from the calculated three-time average value using the following formula (1).

Peptide reduction percentage (%)=(three-time average value of peak heights of peptide in specimen solution/three-time average value of peak heights of peptide in reference solution)×100    (1)

The operation from the preparation of the peptide solution through the measurement by the HPLC analysis was performed three times in total, and the three-time average value of the calculated peptide reduction percentages was regarded as an evaluation result. In addition, in the present test, the specimens of a product 1,3-butylene glycol that were compared were tested on the same day from the viewpoint of reproducibility.

(Conditions of HPLC Analysis in Skin Sensitization Test)

Analysis device: Agilent 1260 InfinityII manufactured by Agilent Technologies, Inc.

Detector: Agilent 1260 InfinityII UV-Vis detector G7114A manufactured by Agilent Technologies, Inc.

Detection wavelength: 220 nm

Analysis column: Zorbax SB-C-18 (particle diameter 3.5 μm, inner diameter×length=2.1 mm×10 mm) manufactured by Agilent Technologies, Inc.

Column temperature: 30° C.

Measurement time: 20 min.

Mobile phases:

A 0.1 vol % trifluoroacetic acid aqueous solution

B 0.085 vol % trifluoroacetic acid-acetonitrile solution

Gradient:

A/B=90/10 to 75/25 (10 min.)

A/B=75/25 to 10/90 (1 min.)

A/B=10/90 (2 min.)

A/B=10/90 to 90/10 (0.5 min.)

A/B=90/10 (6.5 min.)

Mobile phase flow rate: 0.35 mL/min.

Sample injection condition: 5 μL

Example 1

(Heating Treatment Step)

100 g of 1,3-butylene glycol manufactured by KH Neochem Co., Ltd. was charged into a three-neck flask and subjected to a heating treatment at an oil bath temperature of 160° C. for one hour.

(Extraction Step)

Next, 98 g of the 1,3-butylene glycol that had been subjected to the heating treatment step, 100 g of water and 100 g of methylcyclohexane were charged into a 500 mL separable flask, stirred at a temperature set to 10° C. and a rotation speed of 500 rotations/minute for 10 minutes, then, placed still for five minutes and phase-separated into a water layer and an organic layer. 100 g of methylcyclohexane was further added to the separated water layer, and the same operation was repeated twice.

(Dehydration with Distillation Step)

Next, the water layer that had been subjected to the extraction step was charged into an eggplant flask and dehydrated and concentrated at an oil bath temperature of 150° C. and 8 kPa for 30 minutes, thereby obtaining 93 g of 1,3-butylene glycol.

(Low-Boiling Fraction Distillation Step)

Low-boiling fraction distillation was performed on 1,3-butylene glycol that had been subjected to the dehydration and concentration with a distillation device equipped with a 20 cm Vigreux fractionator at an oil bath temperature of 120° C. and 1.2 kPa, and a distillate as much as a weight proportion of 2% of the amount of liquid charged was distilled away from the distillation device top. As a result, 87 g of a product 1,3-butylene glycol was obtained.

As a result of performing the HPLC analysis on the obtained product 1,3-butylene glycol according to the above-described measurement conditions, the sum area value of the absorbance peaks that appeared within the relative retention time range of 4.4 to 12.0 was 453. In addition, it was confirmed by the above-described confirmation method that dinitrophenylhydrazine derivatives of carbonyl compounds having 4 to 6 carbon atoms were contained as components that corresponded to the peaks that appeared within the relative retention time range of 4.4 to 12.0.

As a result of performing the GC analysis according to the above-described measurement conditions, the area percentage of the peak of 1,3-butylene glycol was 99.71%.

As a result of performing the odor test on the product 1,3-butylene glycol, the grade of the odor was one, and the grade of the odor recurrence was two. In addition, as a result of performing the skin sensitization test, the peptide reduction percentage three-time average value was 6.6%. These results relating to the product 1.3-butylene glycol are shown in Table 1.

Example 2

The steps, the analyses and the tests were performed in the same manner as in Example 1 except that methyl isobutyl ketone was used as an extraction solvent in the extraction step and the temperature of the heating treatment step was set to 140° C. As a result of performing the HPLC analysis on the obtained product 1,3-butylene glycol according to the above-described measurement conditions, the sum area value of the absorbance peaks that appeared within the relative retention time range of 4.4 to 12.0 was 104. In addition, it was confirmed by the above-described confirmation method that dinitrophenylhydrazine derivatives of carbonyl compounds having 4 to 6 carbon atoms were contained as components that corresponded to the peaks that appeared within the relative retention time range of 4.4 to 12.0.

As a result of performing the GC analysis according to the above-described measurement conditions, the area percentage of the peak of 1,3-butylene glycol was 99.87%.

As a result of performing the odor test on the product 1,3-butylene glycol, the grade of the odor was one, and the grade of the odor recurrence was one. In addition, as a result of performing the skin sensitization test, the peptide reduction percentage three-time average value was 6.2%. These results relating to the product 1,3-butylene glycol are shown in Table 1.

Comparative Example 1

The steps, the analyses and the tests were performed in the same manner as in Example 1 except that the hydration treatment step and the low-boiling fraction distillation step were not performed and methyl isobutyl ketone was used as the extraction solvent in the extraction step. The details will be described below.

(Extraction Step)

100 g of 1,3-butylene glycol manufactured by KH Neochem Co., Ltd., 100 g of water and 100 g of methyl isobutyl ketone were charged into a 500 mL separable flask, stirred at a temperature set to 10° C. and a rotation speed of 500 rotations/minute for 10 minutes, then, placed still for five minutes and phase-separated into a water layer and an organic layer. 100 g of Methyl isobutyl ketone was further added to the separated water layer, and the same operation was repeated twice.

(Dehydration with Distillation Step)

Next, the water layer obtained in the extraction step was charged into an eggplant flask and dehydrated and concentrated at an oil bath temperature of 150° C. and 8 kPa for 30 minutes, thereby obtaining 79 g of 1,3-butylene glycol.

As a result of performing the HPLC analysis on the 1,3-butylene glycol obtained by the dehydration with distillation step according to the above-described measurement conditions, the sum area value of the absorbance peaks that appeared within the relative retention time range of 4.4 to 12.0 was 1382.

As a result of performing the odor test on the obtained 1,3-butylene glycol, the grade of the odor was three, and the grade of the odor recurrence was four. In addition, as a result of performing the skin sensitization test, the peptide reduction percentage three-time average value was 8.7%. These results relating to 1.3-butylene glycol are shown in Table 1.

TABLE 1

| | | Example 1 | Example 2 | Comparative examples 1 |
|---|---|---|---|---|
| HPLC analysis (sum area value) | | 453 | 104 | 1382 |
| Odor test | Odor (grade) | 1 | 1 | 3 |
| | Odor recurrence (grade) | 2 | 1 | 4 |
| Skin sensitization test | Peptide reduction percentage three-time average value (%) | 6.6 | 6.2 | 8.7 |

The present application is based on a Japanese patent application filed on Jun. 4, 2021 (Japanese Patent Application No. 2021-094284), the content of which is incorporated herein by reference.

INDUSTRIAL APPLICABILITY 1,3-Butylene glycol of the present invention is industrially available as a raw material of synthetic resins, a raw material of surfactants, a solvent, an antifreeze, a cosmetic raw material or the like.

The invention claimed is:

1. A product 1,3-butylene glycol, wherein, in an HPLC analysis under the following conditions after the following sample preparation, when a relative retention time of 2,4-dinitrophenylhydrazine is regarded as 1.0, a sum area value of absorbance peaks that appear within a relative retention time range of 4.4 to 12.0 is 1000 or less, and wherein a dinitrophenylhydrazine derivative of a carbonyl compound having 4 to 6 carbon atoms is contained as a component that corresponds to the peaks that appear within the relative retention time range of 4.4 to 12.0, wherein the sample preparation is as follows:

1000 µL of a solution of 2,4-dinitrophenylhydrazine which is extracted by adding 5 mL of acetonitrile to a 2,4-dinitrophenylhydrazine cartridge and 100 µL of 0.2 mol/L hydrochloric acid are added to 0.05 g of the product 1,3-butylene glycol and reacted at 45° C. for two hours, and wherein the conditions of HPLC analysis are as follows:

measurement sample: a reaction liquid obtained by the sample preparation is diluted to 2 mL with a mobile phase that is used in HPLC, and the diluted liquid is used as a measurement sample, detector: UV-Vis detector, detection wavelength: 369 nm, analysis column: a column in which palmitamidopropyl group-modified silica gel (particle diameter: 5 µm, inner diameter×length=4.6 mm×25 cm, pore size: 100 Å, surface coating level: 2.7 µmol/m$^2$, surface area: 450 m$^2$/g, metal impurity: less than 5 ppm, carbon content: 19.5%) is used as a stationary phase, analysis condition: column temperature of 40° C., mobile phase: acetonitrile/distilled water=50/50 (volume ratio), mobile phase flow rate: 0.4 mL/min., sample injection amount: 20 µL.

2. The product 1,3-butylene glycol according to claim 1, wherein the sum area value of the absorbance peaks that appear within the relative retention time range of 4.4 to 12.0 is 800 or less.

3. The product 1,3-butylene glycol according to claim 1, wherein the sum area value of the absorbance peaks that appear within the relative retention time range of 4.4 to 12.0 is 500 or less.

* * * * *